US010072106B2

(12) United States Patent
Mizrahi et al.

(10) Patent No.: US 10,072,106 B2
(45) Date of Patent: Sep. 11, 2018

(54) N-HALAMINE MELAMINE DERIVATIVES AS NOVEL DECONTAMINATION AND BIOCIDAL AGENTS

(71) Applicant: State of Israel Prime Minister's Office Israel Institute For Biological Research, Nes-Ziona (IL)

(72) Inventors: Dana M. Mizrahi, Rishon LeZion (IL); Ishay Columbus, Efrat (IL)

(73) Assignee: State of Israel, Prime Minister's Office, Israel Insitute For Biological Research, Nes-Ziona (IL)

( * ) Notice: Subject to any disclaimer, the term of this patent is extended or adjusted under 35 U.S.C. 154(b) by 0 days.

(21) Appl. No.: 15/294,445

(22) Filed: Oct. 14, 2016

(65) Prior Publication Data

US 2018/0105618 A1 Apr. 19, 2018

(51) Int. Cl.

| | |
|---|---|
| ***C08F 20/60*** | (2006.01) |
| ***C07D 251/70*** | (2006.01) |
| ***A01N 43/64*** | (2006.01) |
| ***C08G 71/02*** | (2006.01) |
| ***C07D 403/14*** | (2006.01) |
| ***C09D 175/04*** | (2006.01) |
| ***C09D 5/14*** | (2006.01) |
| ***A62D 3/38*** | (2007.01) |
| ***C02F 1/76*** | (2006.01) |
| *A62D 101/02* | (2007.01) |
| *A62D 101/22* | (2007.01) |

(52) U.S. Cl.

CPC .............. *C08F 20/60* (2013.01); *A01N 43/64* (2013.01); *A62D 3/38* (2013.01); *C02F 1/76* (2013.01); *C07D 251/70* (2013.01); *C07D 403/14* (2013.01); *C08G 71/02* (2013.01); *C09D 5/14* (2013.01); *C09D 175/04* (2013.01); *A62D 2101/02* (2013.01); *A62D 2101/22* (2013.01); *C02F 2305/02* (2013.01)

(58) Field of Classification Search

CPC ...... C02F 1/76; C02F 2305/02; C07D 251/70; C08F 20/60; C08G 71/02; C09D 5/14

See application file for complete search history.

(56) References Cited

U.S. PATENT DOCUMENTS

| | | | | |
|---|---|---|---|---|
| 2,472,361 | A | 6/1949 | Arsem | |
| 2,885,305 | A | 5/1959 | Speck, Jr. et al. | |
| 3,438,916 | A * | 4/1969 | Rogers .................. | C08G 18/87 528/288 |
| 4,874,532 | A | 10/1989 | Worley | |
| 6,096,244 | A | 8/2000 | Graichen | |

FOREIGN PATENT DOCUMENTS

| | | | |
|---|---|---|---|
| EP | 0541966 A2 * | 5/1993 | .......... C07D 251/18 |
| IL | 234250 | 2/2016 | |

OTHER PUBLICATIONS

Hui, F. et al. "Antimicrobial N-Halamine Polymers and Coatings: A Review of Their Synthesis, Characterization, and Applications" Biomacromolecules 2013, 14, 585-601.*

Worley, S. D. and Wojtowicz, J. A. 2004. "*N-Halamines*". Kirk-Othmer Encyclopedia of Chemical Technology. http://onlinelibrary.wiley.com/doi/10.1002/0471238961.0308121523151020.a01.pub2/abstract.

Shih, Ming L.et al, "*Analysis and Stability of the Candidate Sulfur Mustard Decontaminant S-330*". Journal of Applied Toxicology, 1999, 19, pp. S89-S95, John Wiley & Sons, Ltd.

Yang, Yu-Chu et al., "*Decontamination of Chemical Warfare Agents*". Chem. Rev. 1992, 92, pp. 1729-1743, American Chemical Society.

Boone, DR. C.M., "*Present state of CBRN decontamination methodologies*". TNO Report, TNO Defence, Security and Safety, TNO-DV 2007 A028, pp. 1-27, Netherlands Organisation for Applied Scientific Research.

Hui, Franck et al., "*Antimicrobial N-Halamine Polymers and Coatings: A Review of Their Synthesis, Characterization, and Applications*". Biomacromolecules, 2013, 14, pp. 585-601, American Chemical Society.

Sun, Gang et al, "*The Chemistry of Functional Finishing: Self-decontaminating Textile Materials*". NTC Project CO2-CD06, Nov. 2004, pp. 1-6, National Textile Center Annual Report.

Fei, Xin and Sun, Gang, "*Oxidative Degradation of Organophosphorous Pesticides by N-Halamine Fabrics*". Ind. Eng. Chem. Res., 2009, 48, pp. 5604-5609, American Chemical Society.

Ren, Xuehon et al., "*N-Halamine-coated cotton for antimicrobial and detoxification applications*". Carbohydrate Polymers, 78, 2009, pp. 220-226, Elsevier Ltd.

Bann, Bernard and Miller, Samuel A., "*Melamine and Derivatives of Melamine*". Aug. 2, 1957, pp. 131-172, British Oxygen Research and Development Ltd., London, England.

"*Determination of the Available Chlorine in Hypochlorites*", Oxidation and Reduction Processes Involving Iodine: Iodometric Titrations, Vogel'S Textbook of Quantitative Chemical Analysis, 1978, Fifth Edition, pp. 396-397, Longman Group UK Limited, Copublished in the United States with John Wiley and Sons Inc.

Mizrahi, Dana M. and Columbus, Ishay, "*P MAS NMR: A Useful Tool for the Evaluation of VX Natural Weathering in Various Urban Matrixes*". Environ. Sci. Technol., 2005, 39, pp. 8931-8935, American Chemical Society.

Mizrahi, Dana M. et al., "*Long-Term Evaluation of the Fate of Sulfur Mustard on Dry and Humid Soils, Asphalt, and Concrete*". Environmental Science and Technology, 2011, 45, pp. 3466-3472, American Chemical Society.

Columbus, Ishay et al., "*VX Fate on Common Matrices: Evaporation versus Degradation*". Environ. Sci. Technol., 2012, 46, pp. 3921-3927, American Chemical Society.

Reiff, Louis P., "*Synthesis of $^{13}$ C Labeled Mustard (HD)*". U.S. Army Edgewood Research, Development and Engineering Center, pp. 799-802. University of Delaware Department of Chemistry and Biochemistry.

(Continued)

*Primary Examiner* — Andrew S Rosenthal

(74) *Attorney, Agent, or Firm* — Venable LLP; Jeffri A. Kaminski

(57) ABSTRACT

The present disclosure relates to the field of decontamination and biocidal agents. More specifically, the invention relates to novel N-halamine melamine derivatives, compositions comprising them, processes for their production, and methods using the same.

10 Claims, 7 Drawing Sheets

(56) References Cited

OTHER PUBLICATIONS

Dubey, D. K. et al., "*Reaction of Bis(2-chloroethyl) Sulfide with N,N'-Dichlorobis(2,4,6-trichlorophenyl) urea*". J. Org. Chem. 1999, 64, pp. 8031-8033, American Chemical Society.
Bartram, Philip W. et al. "*Preliminary Studies on the Decomposition of Bis (2-Cholorethyl) Sulfide Absorbed on Vermiculite*". Research & Technology Directorate, U.S. Army Edgewood Research, Development, and Engineering Center, pp. 623-627.
Sun, Gang, *Biocidal Technology for Reusable and Disposable Textiles*. Division of Textiles and Clothing, University of California, Davis, Oct. 8, 2007.
Shih, Ming L. et al., "*Reactions of Sulfides with S-330, a Potential Decontaminant of Sulfur Mustard in Formulations*". Journal of Applied Toxicology, 19, 1999, pp. S83-S88, John Wiley & Sons, Ltd.

* cited by examiner

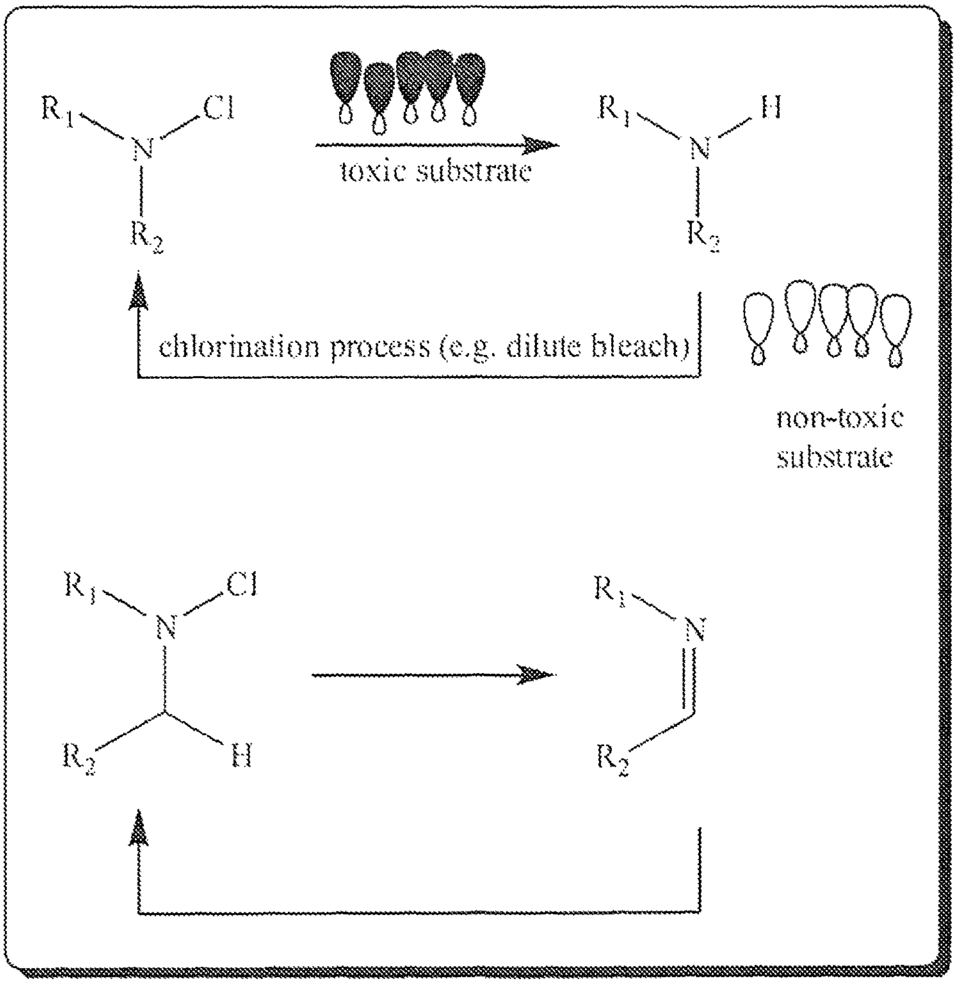
FIG. 1 (PA)

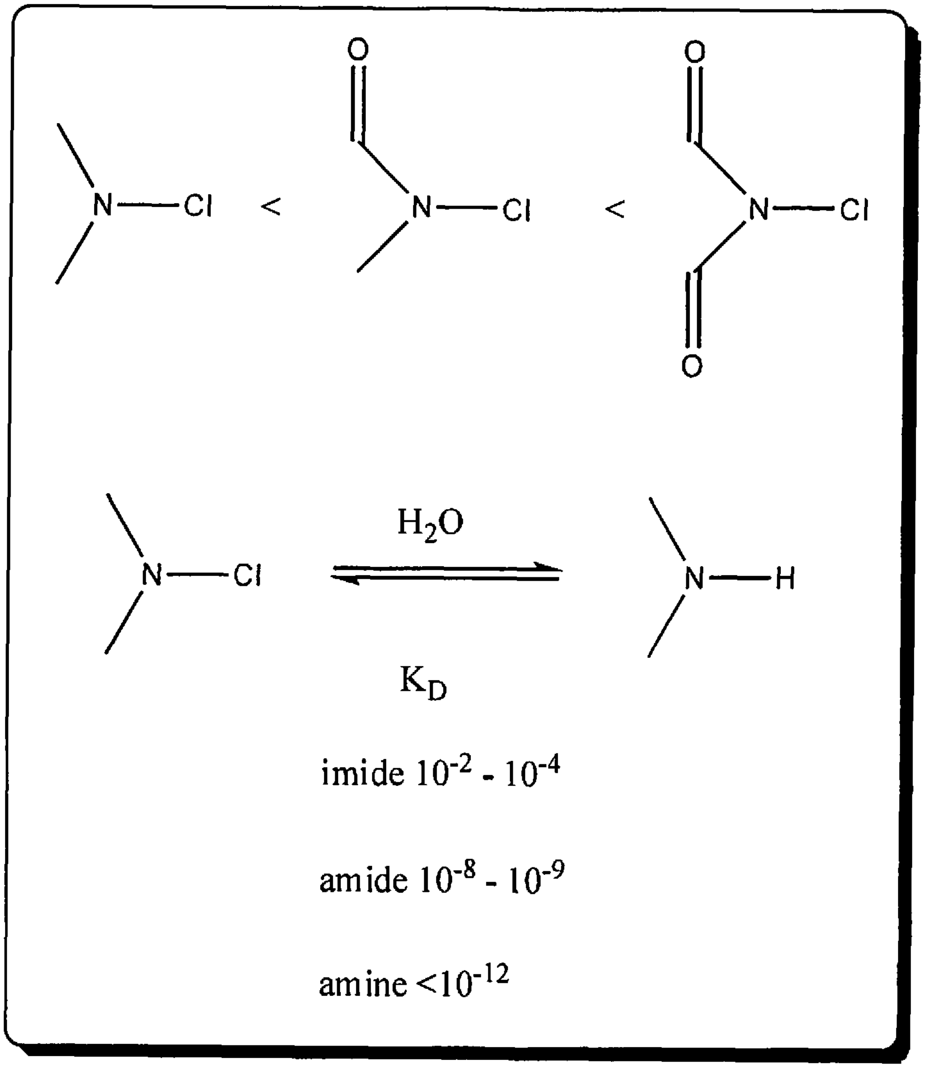
*FIG. 2 (PA)*

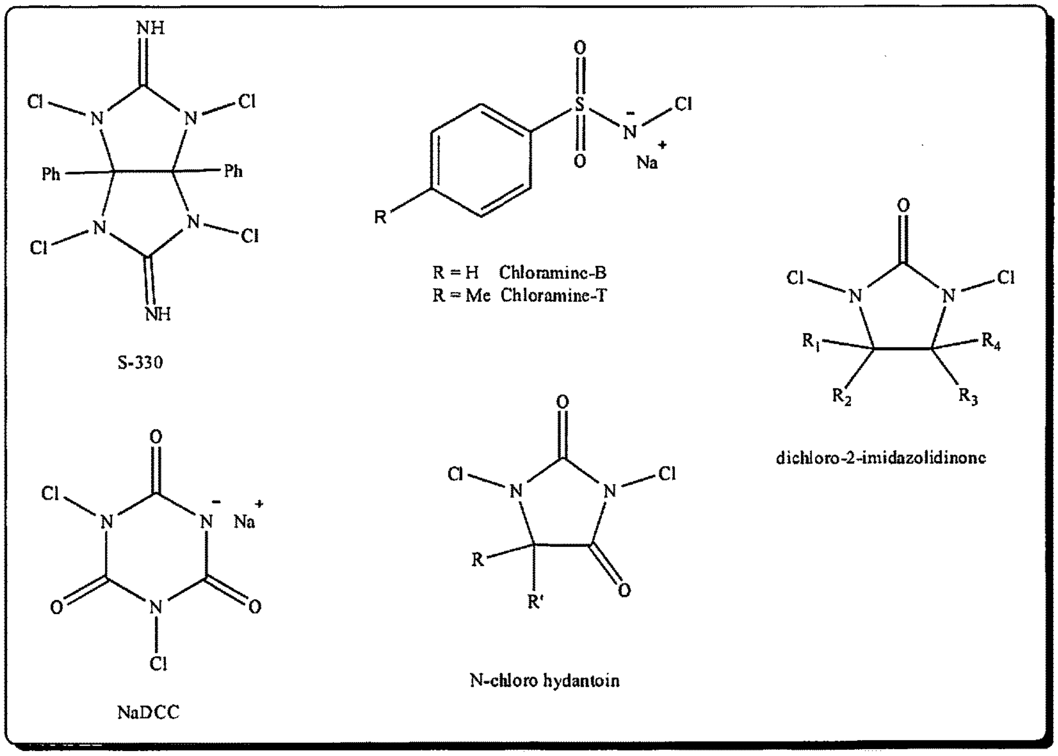
S-330
R = H Chloramine-B
R = Me Chloramine-T
dichloro-2-imidazolidinone
NaDCC
N-chloro hydantoin
FIG. 3 (PA)

N-HALAMINE MELAMINE DERIVATIVES AS NOVEL DECONTAMINATION AND BIOCIDAL AGENTS

FIELD OF THE INVENTION

The present invention relates to the field of decontamination and biocidal agents. More specifically, the invention relates to novel N-halamine melamine derivatives, compositions comprising them, processes for their production, and methods using the same.

BACKGROUND OF THE INVENTION

N-halamines are a family of compounds characterized by a halogen-nitrogen bond (FIG. 1), formed by the reaction of amines, amides or imides with halogen, hypohalous acid or hypohalite [1]. The nature of the halogen in these compounds is formally positive, and thus they exhibit oxidative properties, similar to hypohalous acids and salts (e.g. hypochlorite bleach, NaOCl). The most stable compounds are chloramines and bromamines, which have exhibited diverse reactions and have been widely used for research and industry, especially in the field of water treatment and disinfection. Lately, halamines were attached to polymers and textile for potential use as water purification systems (columns, filters) and biocidal coatings. The main advantage of N-halamine filters and coatings is the optional regeneration of the N—Cl bond after oxidation of the substrate, by hypochlorite wash. This regeneration, however, is possible only if the N—Cl is not adjacent to a C—H bond, since elimination might occur, resulting in loss of N—H capable of being chlorinated (FIG. 1). N—Cl bond strength, indirectly proportional to active chlorine release, is different among chloramines derived from amines, amides and imides (FIG. 2).

As oxidative antibacterial agents, N-halamines have been widely-used for sanitation of pools, spas and water reservoirs, and as additives in laundry products and dishwasher detergents, of which examples will follow. However, only few of the halamines have been employed for decontamination of chemical warfare agents (CWAs), specifically sulfur mustard (HD) and VX ([S-2-(diisopropylamino) ethyl]-O-ethyl methylphosphonothiolate), which are sensitive to oxidation.

Tetrachlorinated glycolurils have been developed and tested as protection against chemical agents back in the 1950s and 1960s [2], and continue to exhibit interesting results to date, as candidates for sulfur mustard decontamination. A promising candidate, S-330 (FIG. 3), was evaluated as an anti-vesicant additive for a topical skin protectant [3]. Chlorinated hydantoins and imidazolidinones (FIG. 3) were also employed for the decontamination of toxic chemicals, usually evaluated against sulfur mustard simulants [4]. N-chlorosulfonamidates, chloramine-B and chloramine-T, (FIG. 3) were used to oxidize sulfur mustard and VX, as a part of a Soviet personal decontamination kit, adopted later in the American M258 kit. This reaction took place in an aqueous/alcoholic solution containing 5% $ZnCl_2$ to maintain a pH of 5-6 [5]. However, at this low pH, detoxification of G-agents was not efficient. Nowadays, these compounds and their respective dichloramines (a second Cl atom instead of the Na) are used, as a mixture with hexachloromelamine 1 in a Russian decontamination solution for vehicles and terrain. A pool-sanitizing compound, sodium dichloroisocyanurate (NaDCC, FIG. 3) has been employed in CWA decontamination as the active ingredient of various products (Cristanini's BX-24, OWR's 10% NaDCC aqueous solution for terrain decontamination, OWR's BC emulsion and CASCAD). In contrast to former N-halamines, NaDCC is used specifically for terrain rather than personal decontamination [6].

Lately, a comprehensive review of halamines and their applications has been published [7]. Most of the current synthetic efforts in the N-halamine field have been directed at the attachment of N-halamines to insoluble polymers, thus obtaining antibacterial fabrics, active resins, filters and columns suitable for antibacterial water treatment. Decontamination of CWAs and simulants was also addressed by polymeric N-halamines, preferably hydantoins (FIG. 3) attached to fabrics. These studies include grafting of hydantoin monomers on synthetic fibers [8], direct attachment of hydantoin methylols on cotton or cotton/polyester [9] or attachment of hydantoins to cotton via a siloxane bond [10]. Notwithstanding, the majority of polymeric N-halamine products address bacteria and other biological hazards, rather than deal with chemical agent decontamination.

Current decontaminating agents focus on treating the CWA available for decontamination, such as visible droplets on contaminated surfaces. However, a substantial amount of CWA penetrates polymeric surfaces within a short while post contamination (~30-40% in 30 min). This fraction is not available for destruction by current (mostly aqueous) decontamination agents. Hence, the contaminated polymeric surfaces pose a long-term hazard. Therefore, there is currently a need for novel efficient decontamination agents for CWA and/or biological agent absorbed into polymeric matrices such as paint, coatings, and plastics.

Therefore, it is an object of the present invention to provide novel chemical compounds capable of overcoming the drawbacks of existing decontamination and biocidal agents, and which can be incorporated into polymeric matrices to provide self-decontaminating surfaces. The self-decontaminating surfaces of the invention are capable of both efficiently deactivating any CWA and neutralizing any biological agent which penetrates the surface after exposure.

It is another object of the invention to provide novel decontamination agents that may be advantageously used as additives in various chemical compositions.

It is a further object of the invention to provide processes for manufacturing novel compounds active as decontamination and biocidal agents as well as methods of using the same.

Further purposes and advantages of this invention will appear as the description proceeds.

SUMMARY OF THE INVENTION

The present invention provides a multihalogenated N-halamine compound or any salt thereof, comprising at least one halogenated melamine derivative. In a particular embodiment, the compound is selected from the group consisting of compounds of formula (I), (II), (III), (IV), and (V):

(I)

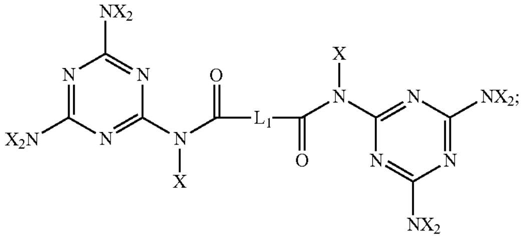

;

-continued (II)

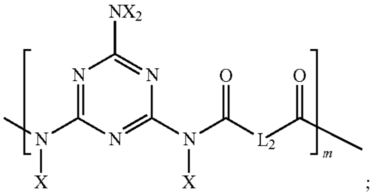

;

(III)

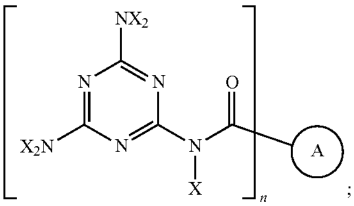

;

(IV)

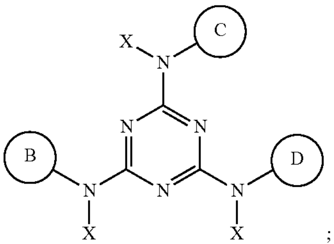

;

(V)

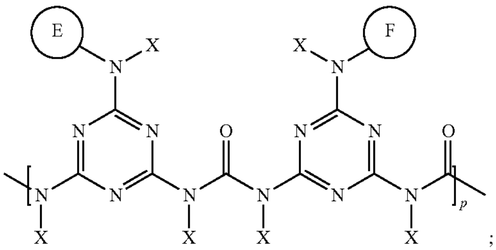

;

wherein

A is selected from optionally substituted cycloalkyl, heterocyclyl, aryl, and heteroaryl;

B, C and D are independently selected from hydrogen, halogen, optionally substituted —C(═O)-alkenyl, —C(═O)-alkynyl, —$CH_2$-alkyl, —$CH_2$-alkenyl, and —$CH_2$-alkynyl, provided that at least one of B, C or D is not hydrogen or X;

E and F are independently selected from hydrogen, halogen, —C(═O)—N(halogen)-melamine;

X is a halogen selected from Cl, Br, I and F;

$L_1$ and $L_2$ are linkers independently selected from optionally substituted alkyl, alkylene, alkynyl, heteroalkyl, heteroalkylene, and heteroalkynyl; and m, n, p are selected from 1 to 20.

In another embodiment, the compound of the invention (or a salt thereof) is selected from the group consisting of the following formulae:

(I′)

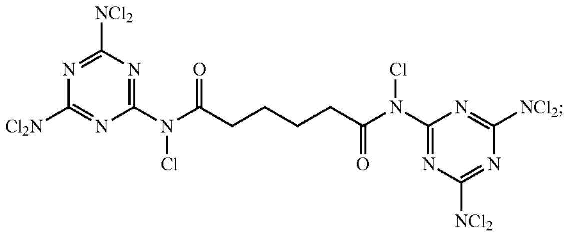

(I″)

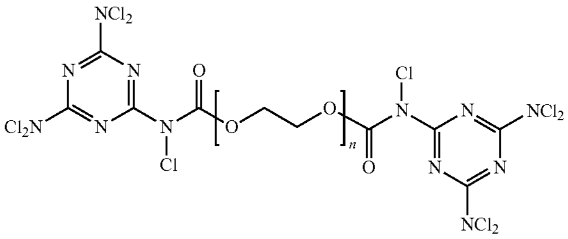

n = 2-20
n = 3-21 wherein n is 2 or 3;

(II)

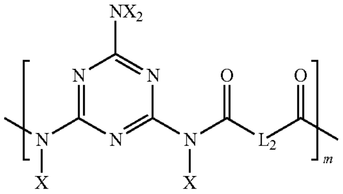

wherein $L_2$ is —$(CH_2)_4$— or —$[O(CH_2)]_3O$—;

(III′)

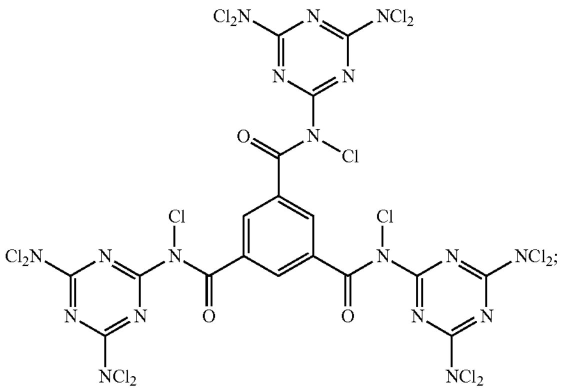

-continued (III″)

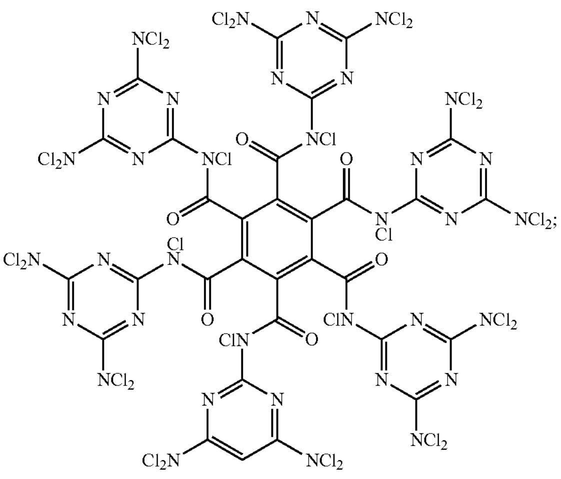

(IV′)

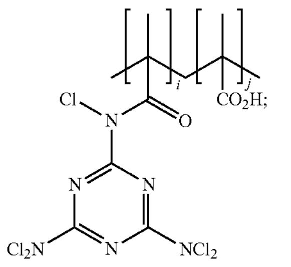

wherein i and j are selected from 1 to 20

(IV″)

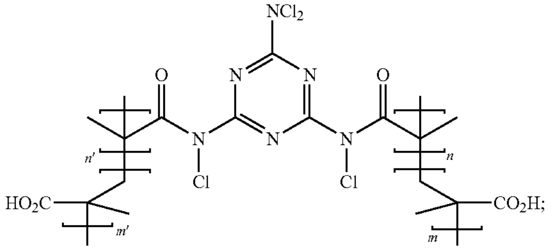

wherein i, j, i' and j' are selected from 1 to 20;

(V′)

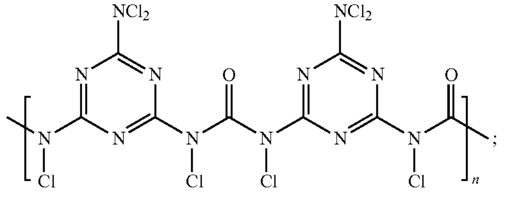

wherein n is selected from 1 to 20;

(V″)

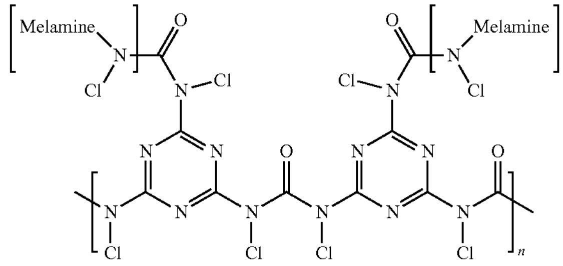

wherein n is selected from 1 to 20.

In some specific embodiments, the compound of the invention has a percentage of active halogen of between 10% and 90%, 20% and 80%, 30% and 70%, or 40% and 60%. In some other specific embodiments, the N-halamine bonds are regenerated by contacting said compound with hypochlorite, hypobromite, hypoiodite, or hypofluorite.

The invention further provides a micro- or nano-particle/structure coated with or covalently bound to a compound as defined above or a salt thereof.

The invention still further provides a composition comprising a compound as defined above or a salt thereof and at least one ingredient selected from the group consisting of solvents, diluents, binders, resins, polymers, fillers, pigments, dyes, wetting agents, catalysts, thickeners, stabilizers, emulsifiers, texturizers, adhesion promoters, UV stabilizers, flatteners, and biocides. In some particular embodiments, said composition is selected from a paint, a plastic material, a silicone-based material, a textile, or a coating. In some specific embodiments, said composition is for use in columns for water treatment. In some specific embodiments, the polymer is selected from the group consisting of polystyrene, polyamide, polyethyleneimine, polycarbonate, polyolefis, styrene-acrylonitrile, acrylonitrile-butadiene-styrene, polyester, polyurethane, epoxide, polyphenylene ether, halogen-substituted organic polymer, phthalic acid amide, polyphenylene sulfide, liquid crystal polymers, polyethylene terephthalate cyclohexane and combinations thereof.

The invention still further provides a compound, a salt thereof, or a composition comprising the same, for use as a decontaminating agent for deactivating a chemical agent and/or neutralizing a biological agent. In some particular embodiments, said chemical agent is a chemical warfare agent (CWA), more particularly sulfur mustard (HD) or O-ethyl-S-2-(N,N-diisopropylamino)ethylmethylphosphonate (VX). In some other embodiments, said biological agent is a bacterial agent, more particularly, *E. Coli, Staphylococcus Aureus, Bacillus Anthracis*, mold or mildew.

The invention still further provides a method for decontaminating or preventing the contamination of a material by a chemical agent and/or a biological agent, said method comprising incorporating into said material or applying onto said material an effective amount of a compound according to the above, a salt thereof, or a composition comprising the same.

The invention still further provides a method for preventing formation of mould on a material, said method comprising incorporating into said material or coating onto said material an effective amount of a compound according to the above, a salt thereof, or a composition comprising the same.

The invention still further provides a process for manufacturing a compound according to the above, said process comprising at least one of the following steps:

(i) reacting diacid dichloride with monochloromelamine and treating the resulting compound with hypochlorite bleach;
(ii) reacting dicarboxychloride-polyethylene glycol (PEG) with monochloromelamine and treating the resulting compound with hypochlorite bleach;
(iii) reacting diacid chloride with dichloromelamine and treating the resulting compound with hypochlorite bleach;
(iv) reacting 1,3,5-tricarbonyl trichloride benzene with chloromelamine and treating the resulting compound with hypochlorite bleach;
(v) reacting mellitic acid with PCl5 to obtain a hexa acid chloride; reacting said hexa acid chloride with chloromelamine, and treating the resulting compound with hypochlorite bleach;
(vi) reacting methacryloyl chloride with chloromelamine in CCl4, and treating the resulting compound with hypochlorite bleach;
(vii) reacting methacryloyl chloride with dichloromelamine in CCl4, and treating the resulting compound with hypochlorite bleach;
(viii) reacting triphosgene with dichloromelamine, and treating the resulting compound with hypochlorite bleach; and
(ix) reacting triphosgene with trichloromelamine, and treating the resulting compound with hypochlorite bleach.

The invention still further provides a method for manufacturing a self-decontaminating material, said method comprising incorporating into said material a compound according to the above, a salt thereof, or a composition comprising the same.

The invention still further provides a method for manufacturing a melamine-silica particle, said method comprising coating or covalently binding to said silica particle one or more melamine moieties.

The invention still further provides a method for manufacturing a melamine bearing polymer, said method comprising polymerizing one or more melamine derivatives to form said melamine bearing polymer.

BRIEF DESCRIPTION OF THE DRAWINGS

The above and other characteristics and advantages of the invention will be more readily apparent through the following examples, and with reference to the appended drawings, wherein:

FIG. 1 is a scheme showing N—Cl regeneration, when no a-hydrogen is present

FIG. 2 is a scheme showing the reactivity of N—Cl bonds

FIG. 3 shows some known N-halamines involved in chemical warfare agent decontamination

DETAILED DESCRIPTION

Figure 4A:
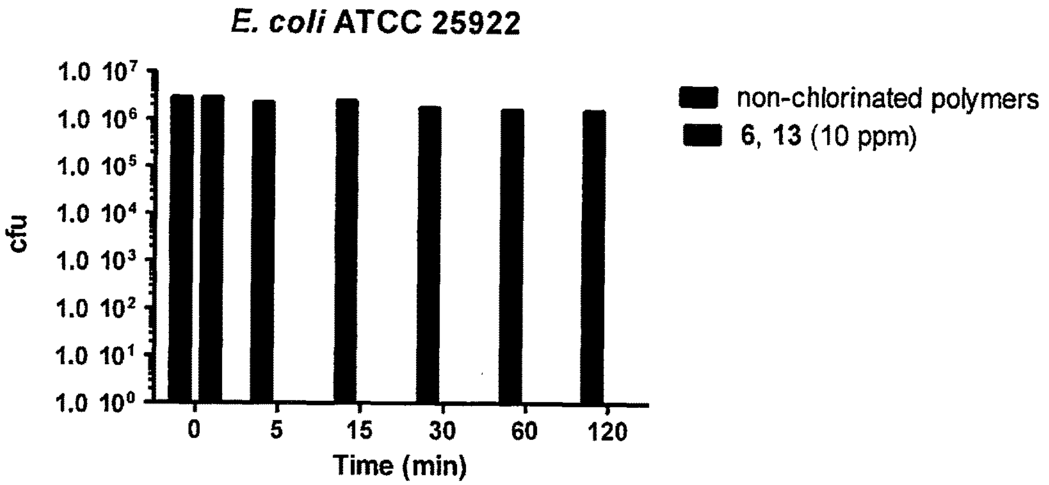
FIGS. 4A and 4B are graphs showing the killing efficiency of the compounds of the invention towards *E. coli* (4A) and *S. aureus* (4B)

The phrase "a" or "an" entity as used herein refers to one or more of that entity; for example, a compound refers to one or more compounds or at least one compound. As such, the terms "a" (or "an"), "one or more", and "at least one" can be used interchangeably herein. [0010] As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R1 appears twice and is defined as "independently carbon or nitrogen", both R1 can be carbon, both R1 can be nitrogen, or one R1 can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

If a substituent is designated to be "absent", the substituent is not present.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "carboxyl" as used herein refers to a group of formula R1—C(═O)R2 wherein each of R1 and R2 is independently hydrogen or a lower alkyl as defined below.

The term "amino" as used herein denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "alkyl" as used herein denotes an unbranched or branched chain, saturated, monovalent hydrocarbon residue containing 1 to 20 carbon atoms. The term "lower alkyl" denotes a straight or branched chain hydrocarbon residue containing 1 to 6 carbon atoms. Lower alkyl groups include methyl, ethyl, propyl, butyl, pentyl, isopentyl, neopentyl, hexyl, heptyl, and octyl. "$C_1$-$C_{20}$ alkyl" as used herein refers to an alkyl composed of 1 to 20 carbons.

The term "alkylene" as used herein denotes a divalent saturated linear hydrocarbon radical of 1 to 20 carbon atoms or a branched saturated divalent hydrocarbon radical of 2 to 20 carbon atoms, unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkynyl" as used herein refers to a radical of a straight-chain or branched hydrocarbon group having from 2 to 20 carbon atoms and one or more carbon-carbon triple bonds (e.g., 1, 2, 3, or 4 triple bonds).

The terms "heteroalkyl", "heteroalkylene", and "heteroalkynyl" as used herein denotes an alkyl, an alkylene or an alkynyl group as defined above which further includes at least one heteroatom (e.g., 1, 2, 3, or 4 heteroatoms) selected from oxygen, nitrogen, or sulfur within and/or placed at one or more terminal position(s) of the parent chain.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "heterocyclyl" denotes a radical of a 3- to 14-membered non-aromatic ring system having ring carbon atoms and 1 to 4 ring heteroatoms, wherein each heteroatom is independently selected from nitrogen, oxygen, and sulfur. In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

The term "aryl" denotes a radical of a monocyclic or polycyclic (e.g., bicyclic or tricyclic) 4n+2 aromatic ring system (e.g., having 6, 10, or 14 a electrons shared in a cyclic array) having 6-14 ring carbon atoms and zero heteroatoms provided in the aromatic ring system. "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" denotes a a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzo furanyl, isothiazolyl, benzothienyl, indolyl, isoindolyl, isobenzo furanyl, benzimidazolyl, benzoxazolyl, benzoisoxazolyl, benzothiazolyl, benzoisothiazolyl, As understood from the above, alkyl, alkenyl, alkynyl, heteroalkyl, heteroalkenyl, heteroalkynyl, cycloalkyl, heterocyclyl, aryl, and heteroaryl groups, as defined herein, are, in certain embodiments, optionally substituted with one or more subsitutents selected from halogen, lower alkyl, carboxyl, hydroxyl, sulfonyl, and amino.

The following examples, which further describe the invention, are offered by way of illustration and are not intended to limit the invention in any manner.

EXAMPLE 1

Chlorinated Melamine

Melamine, 1,3,5-triazine-2,4,6-triamine is an organic base, with vast use, in combination with formaldehyde, as melamine resin in the plastic industry. Melamine has been found particularly advantageous since the amine groups, of guanidine nature, may also serve as handles for attachment to commercial polymers or polymerizable moieties. Moreover, melamine contains three amines that could be converted into 1 to 6 active N—Cl groups. Full chlorination of melamine was carried out by 5% hypochlorite bleach in slightly acidic to neutral pH. Resulting hexachloromelamine (1) served as a chlorinating agent for further reactions. Partially chlorinated melamines 2, 3 and 4 were obtained by disproportionation of chlorine atoms, when hexachloromelamine was mixed and heated with various ratios of melamine (Scheme 1)[11]. These partially chlorinated melamines were used for further conjugation of the melamine moiety.

Scheme 1. Synthesis of chlorinated melamines

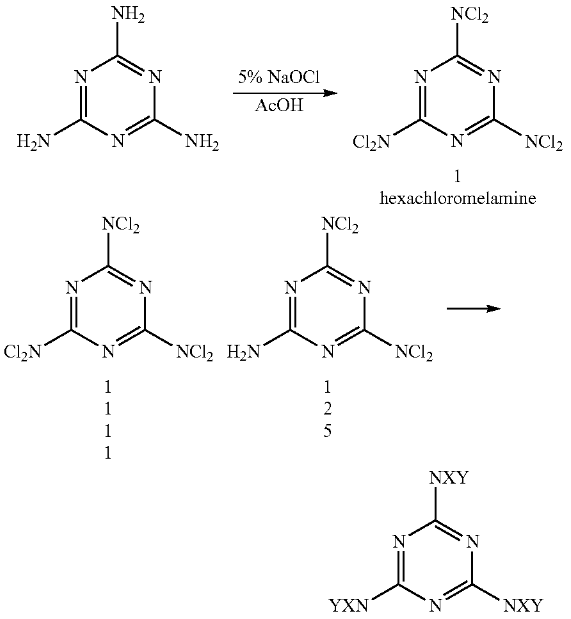

1
hexachloromelamine 1
1
1
1

1
2
5

X, Y = H, Cl

H = Cl = 3 trichloromelamine 2
H = 4; Cl = 2 dichloromelamine 3
H = 5; Cl = 1 monochloromelamine 4

EXAMPLE 2

Melamine Polymethacrylate Derivatives

As a rule, effective CWA decontamination is achieved by large quantities of decontaminant, as compared to the toxic agent. Hence, the preparation of melamine-based polymers, where most of the amine moieties remain available for subsequent chlorination might afford a highly reactive polymer. Another requirement of these polymers was to sustain their ability for regeneration (no a-hydrogen atoms). To accommodate these requirements, we designed a methacryloyl-melamine monomer, where a single polymerization handle is attached via an amide bond to one of the melamine amine groups, while the other two remain free (scheme 2). In a similar manner, more than one methacrylate group may be attached, to form cross-linked polymers.

Acylation of melamine is usually carried out by prolonged heating with the desired acid anhydride or amide, while acid halides seem to have little or no effect on melamine [12]. The use of high temperatures (170-200° C.), combined with large amounts of acid derivatives (usually serving as solvents), gives rise to di- and tri-amides of melamine in many cases [13].

A more recent work described the preparation of melamine amides directly from halogenated melamines. In comparison to standard amide formation, where an acid chloride reacts with an amine to form an amide while releasing HCl, the proposed reaction between an acid halide and chloromelamine forms the desired amide while releasing Cl, (scheme 2) [14]. Although this work dealt with the formation of tris amides and tris carbamates, the relatively mild conditions (75° C., 3 h) prompted us to attempt monoamidation by the reaction of monochloromelamine 4 with methacryloyl chloride, to form the desired monomer.

Scheme 2. Preparation of melamine amides form halomelamine

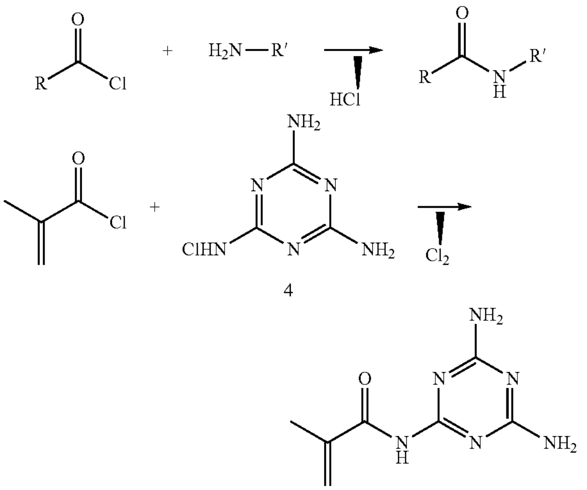

4

The reaction of 4 with one equivalent of methacryloyl chloride in CCI, resulted in partial polymerization of the desired monomer. This could be explained by the release of chlorine radicals in the reaction mixture, upon formation of the amide. These radicals initiated the polymerization process (scheme 3). To verify this, the reaction was repeated in methacryloyl chloride as solvent, for 18 h. The resulting precipitate was proven to consist of methacrylic polymer bearing melamine groups. Thus, in one step, both amidation and polymerization were performed. Due to the fact that this polymerization took place in methacryloyl chloride, the product was a copolymer of melamine methacrylamide and methacryloyl chloride 5.

Copolymer 5 was subjected to chlorination by dilute hypochlorite bleach in slightly acidic pH (5-6). As a result, the amine groups were chlorinated and the acid chloride underwent hydrolysis to the corresponding acid. The chlorinated copolymer 6 was identified by $^{1}$H NMR, $^{13}$C NMR, FTIR-ATR and gave a positive result when placed on a KI-starch paper (strong purple stain). As a rule, melamines, and especially polymelamines, are rather insoluble and could be evaluated in NMR only in DMSO-$d_6$. However, all chlorinated melamines, monomers or polymers alike, exhibited violent exothermic reaction to DMSO-$d_6$ and thus, NMR spectra of the chlorinated molecules could be run only in pyridine-$d_5$.

Scheme 3. Preparation of poly(melamine methacrylamide -co-methacryloyl chloride) and subsequent chlorination

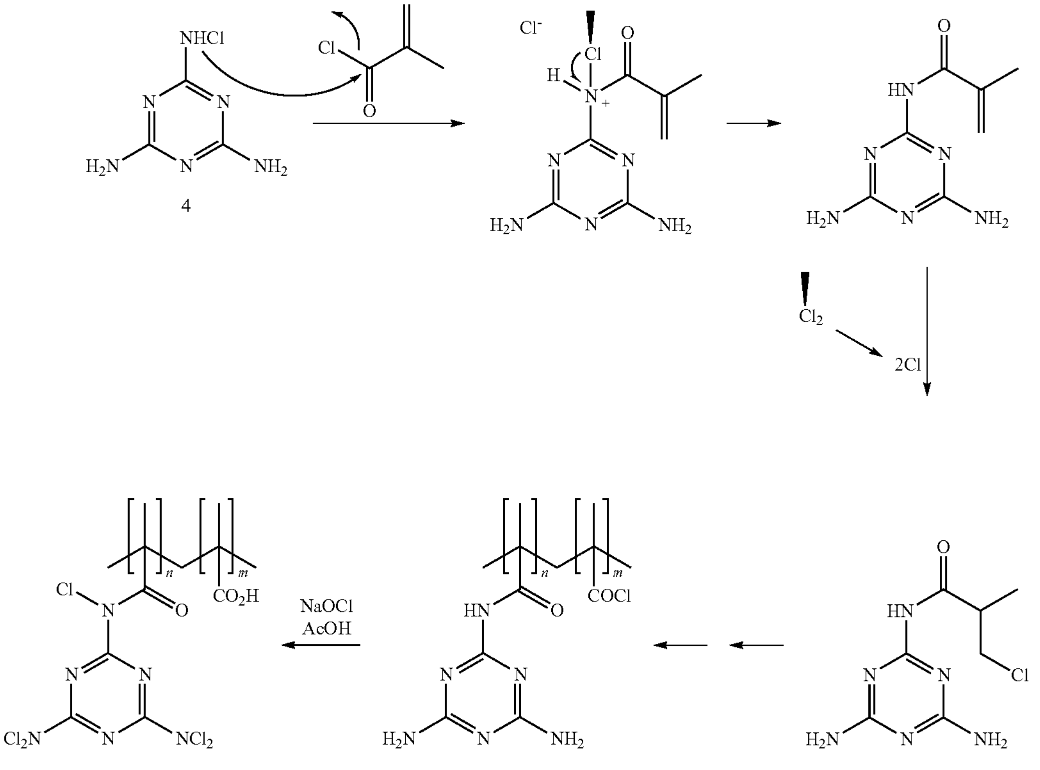

4 5 6

The same conditions were used to prepare a cross-linked polymer based on melamine and methacrylate. In this case, diamidation, followed by polymerization was carried out on dichloromelamine 3, to afford chains of polymethacrylic acid linked by melamine moieties 7, which were later chlorinated to give 8 (scheme 4).

A similar reaction, carried out on trichloromelamine 2, afforded the highly cross-linked polymer 9, which was subsequently chlorinated by hypochlorite bleach in the usual manner to give polymer 10 (scheme 4).

Scheme 4. Preparation of cross-linked melamine-methacrylate polymer

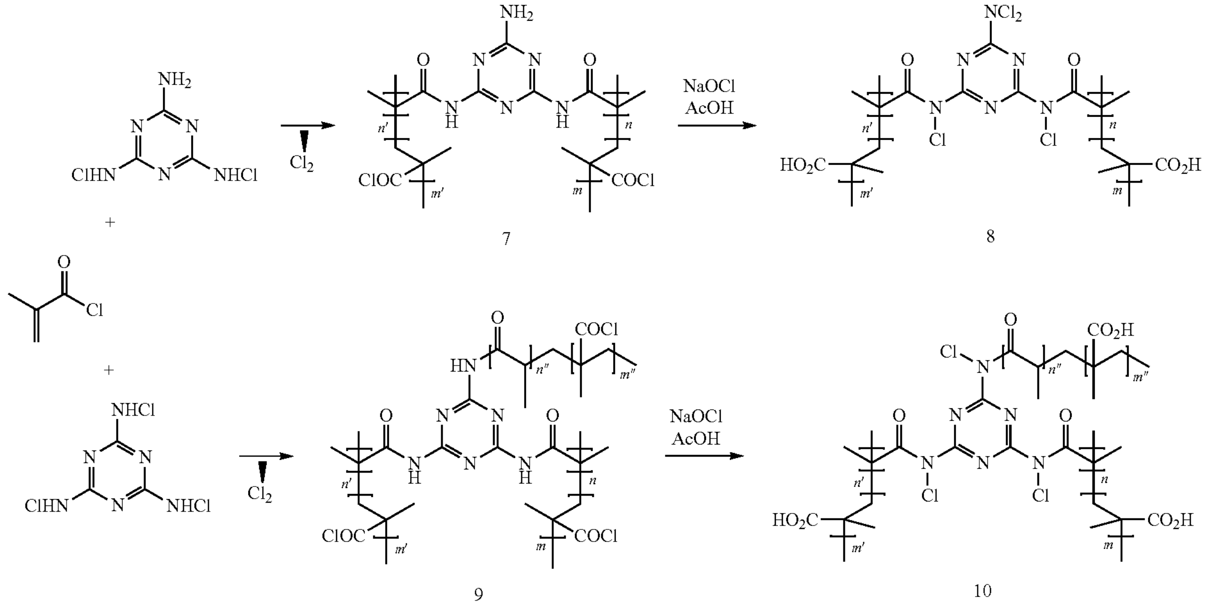

7 8 9 10

In order to study the influence of melamine groups on polymer decontaminating activity, a similar polymer was prepared, based on methacrylamide, whose amide groups were subsequently chlorinated in the same manner (11, scheme 5).

Scheme 5. Preparation of chlorinated poly(methacrylamide)

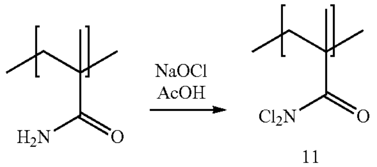

11

EXAMPLE 3

Polyurea Melamine

The general reaction of acid halides with chloromelamines (described in scheme 2) was utilized in the preparation of a novel family of melamine polymers, containing carbonyl groups as linkers between any two melamine moieties. Triphosgene (a stable substitute to phosgene) was reacted with dichloromelamine 3 or trichloromelamine 2 to form a chain polyurea-melamine 12 or branched polyurea-melamine 14, respectively (scheme 6). These polymers were subsequently chlorinated by the usual method to form polymers 13 and 15. These polymers contain a large amount of chlorinated melamines per weight, as compared to the polymethacrylate derivatives, due to the small carbonyl linker.

Scheme 6. Preparation of polyurea-melamines

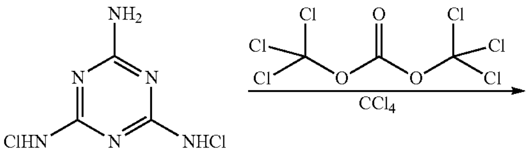

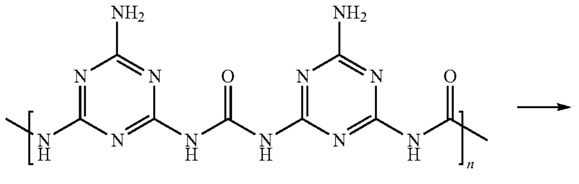

12

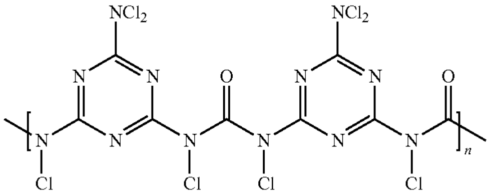

13

-continued

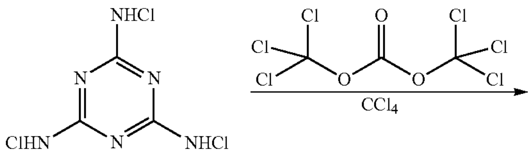

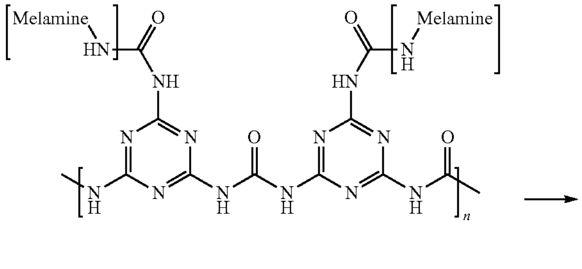

14

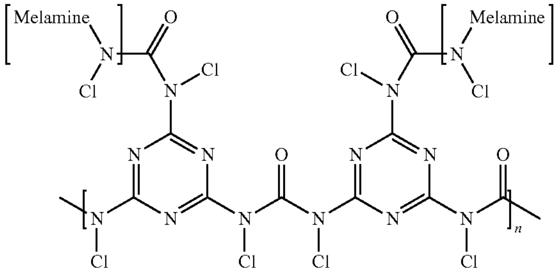

15

EXAMPLE 4

Bis-melamine Derivatives

In general, bismelamines bearing two melamine moieties were prepared by reacting diacid chlorides with two equivalents of monochloromelamine 4, as described before. Among these diacid chlorides: adipoyl dichloride (resulting in bismelamine amide 16 and chlorinated bismelamine amide 17, scheme 7) and two carboxyl chloride-terminated PEGs (resulting in bismelamine carbamates 18 and 19, and chlorinated carbamates 20 and 21, scheme 8). Polymers based on these bismelamines were prepared by the reaction of the diacid chlorides with dichloromelamine 3 (Scheme 9).

Scheme 7. Preparation of bismelamine adipoyl

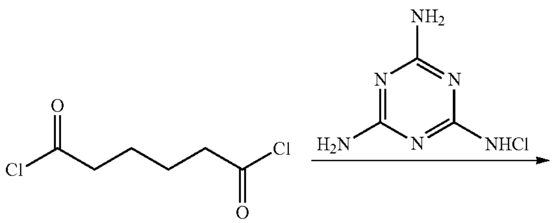

-continued

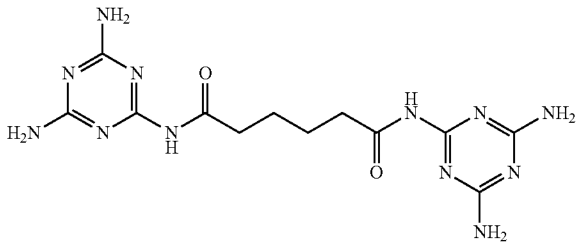

16

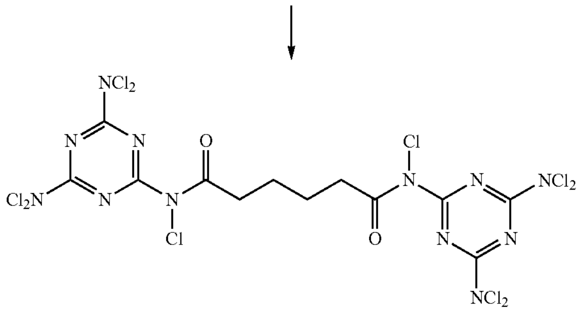

17

Scheme 8. Preparation of bismelamine carbamates

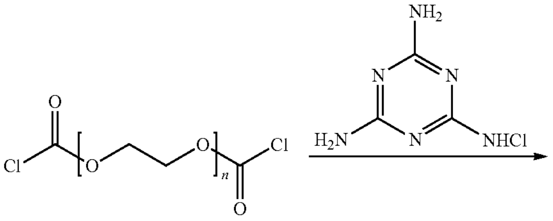

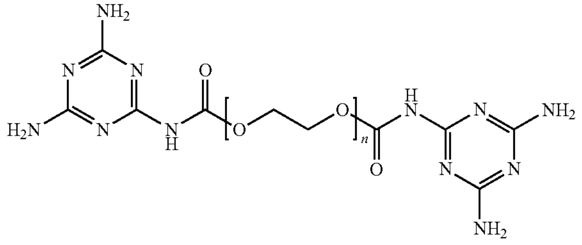

n = 2 18
n = 3 19

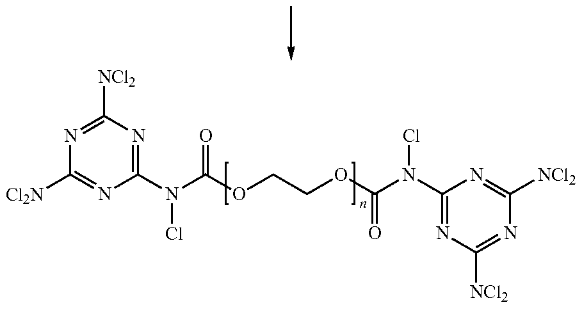

n = 2 20
n = 3 21

Scheme 9. Preparation of linear polymers bearing melamine groups

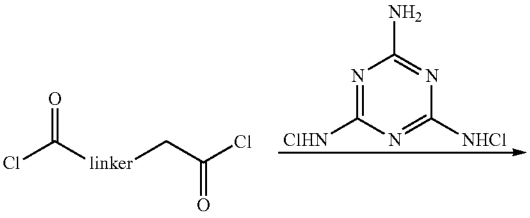

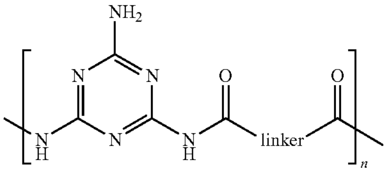

linker = $(CH_2)_4$ 22
linker = $PEG_3$ 23

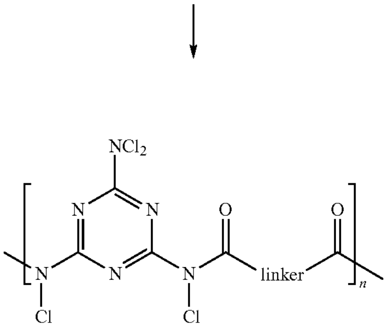

linker = $(CH_2)_4$ 24
linker = $PEG_3$ 25

EXAMPLE 5

Tris-melamine Derivatives

A small molecule bearing three melamine moieties was prepared from 1,3,5-tricarbonyl trichloride benzene, which was reacted in the usual manner with three equivalents of monochloromelamine 4. 1,3,5-tricarbonyl trismelamine-amide 26 was subsequently converted to the chlorinated form 27 by treating with hypochlorite bleach at pH=5 (Scheme 10).

Scheme 10. Preparation of trismelamineamide

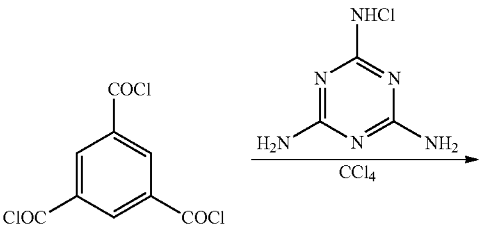

-continued

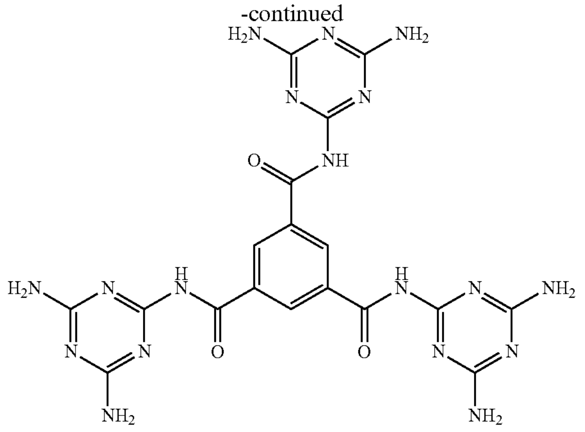

26

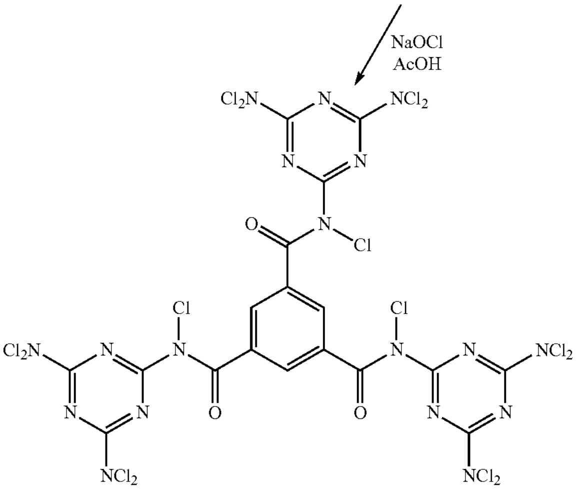

27

EXAMPLE 6

Hexakismelamine

Hexachlorocyclotriphosphazene was used as a starting material to prepare a small molecule with six melamine groups attached to a cyclophosphazene core. The typical procedure that we carried out during this work, namely the reaction of acid chloride with monochloromelamine to form the amide, proved less successful in the case of phosphazene chloride. A maximum of four melamine groups were attached to the core in this reaction. This result repeated itself upon changing solvents, increasing the reaction temperature and duration, and even upon the addition of base.

Finally, the desired hexakismelamine cyclotriphosphazene was prepared by the rather facile reaction of hexachlorocyclotriphosphazene with six equivalents of melamine in boiling water (Scheme 11). Increase in reaction time or starting material concentration resulted in formation of cyclophosphazene-melamine polymers. Unfortunately, the desired product 28 could not be chlorinated, since, under the reaction conditions, the cyclotriphosphazene core collapsed.

Scheme 11. Preparation of hexakismelamine cyclotriphoshazene

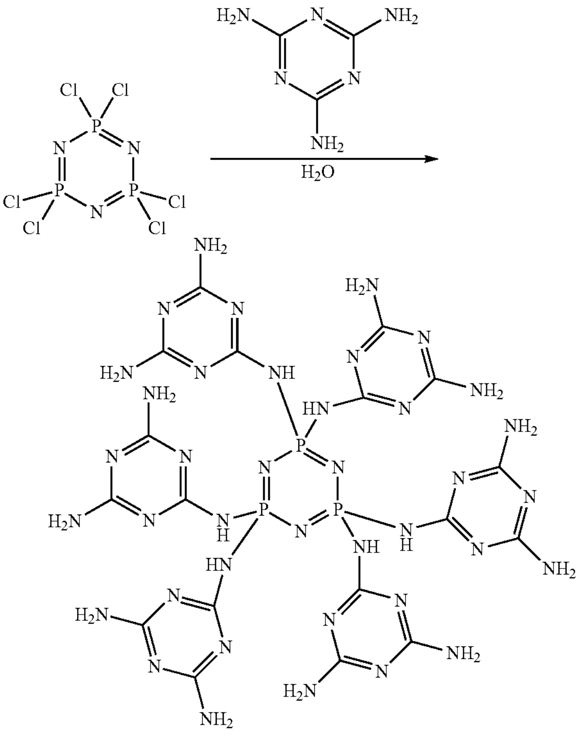

28

A small molecule bearing six melamine moieties was prepared from mellitic acid, which was initially converted into hexa acid chloride with $PCl_5$, and was then reacted in the usual manner with six equivalents of monochloromelamine 4. Benzene hexakismelamineamide 29 was subsequently converted to the chlorinated form 30 by treating with hypochlorite bleach at pH=5 (Scheme 12).

Scheme 12. Preparation of hexakisismelamineamide

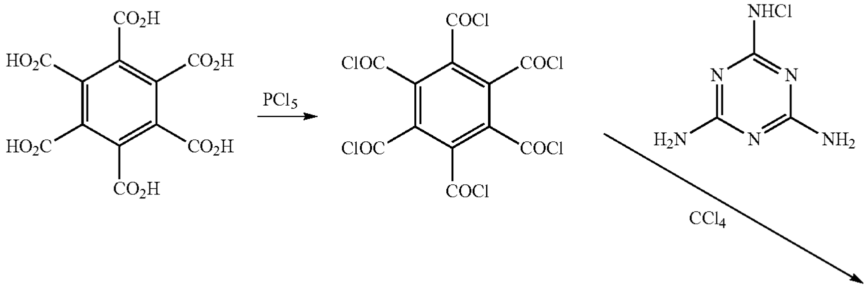

-continued

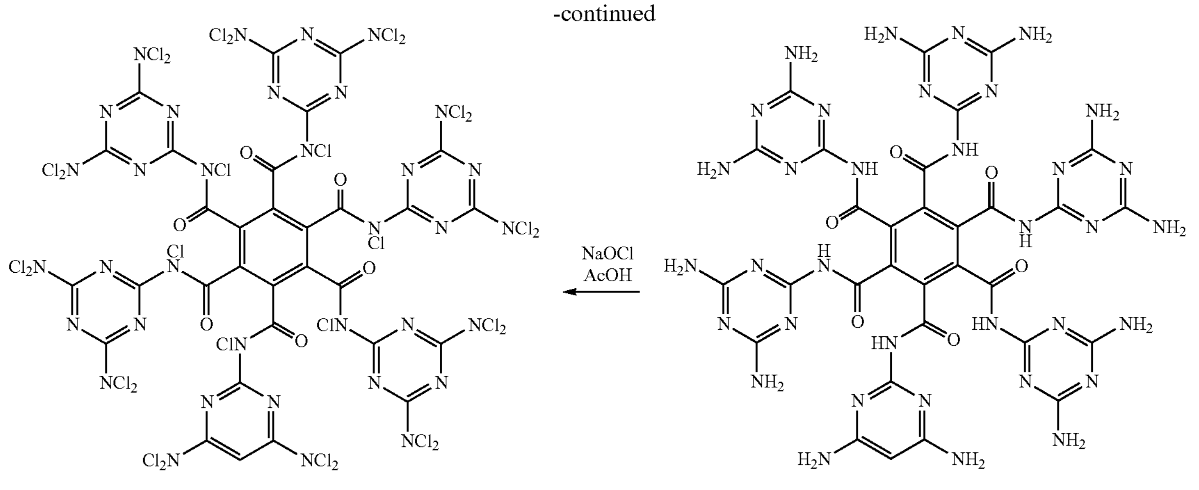

29 30

EXAMPLE 7

Determination of the Available Chlorine in Melamine Halamines

The determination of active chlorine in the synthesized melamine halamines was carried out in the usual manner for the determination of available chlorine in hypochlorite solutions, through iodometric method [15].

The results are displayed in Table 1 (a percentage range denotes several measurements on various batches).

TABLE 1

Active Chlorine Percentage of Chlorinated Compounds

| Compound | % Cl |
|---|---|
| 1 | 38-43% |
| 2 | 31% |
| 3 | 25-27% |
| 4 | 13-14% |
| 6 | 19% |
| 8 | 13% |
| 11 | 13% |
| 13 | 49% |
| 15 | 42% |
| 17 | 56% |
| 20 | 48% |
| 21 | 46% |
| 24 | 50% |
| 25 | 42% |
| 27 | 58% |
| 30 | 41% |

EXAMPLE 8

Decontamination of Chemical Warfare Agents (CWAs)

Caution: These experiments should only be performed by trained personnel using applicable safety procedures. Some of the decontamination reactions are violent and exothermic.

Decontamination of CWAs by melamine halamines was usually evaluated by solid state magic angle spinning (MAS) $^{31}P$ or $^{13}C$ NMR. The halamines were tested against sulfur mustard (HD) and VX (O-ethyl-S-2-(N,N-diisopropylamino)ethyl methylphosphonate), which are susceptible to oxidation. In a typical test [16], the melamine halamine powder (ca. 40 mg) was used to fill a 4-mm $ZrO_2$ rotor. Next, VX or $^{13}C$-labeled HD [17] (2-3 mg, 5-6.5%) were applied directly to the center of the sample. The rotor was sealed with a fitted Kel-F cap. $^{31}P$ (for VX) or $^{13}C$ (for HD) MAS NMR experiments were carried out on a 500 MHz Avance (Bruker) spectrometer equipped with a 4-mm standard CP-MAS probe using direct excitation (no CP). The observation frequency was 202 MHz ($^{31}P$) and 125 MHz ($^{13}C$). Remaining CWA quantity and decontamination products were determined.

In cases where decontamination reactions were violent, the reaction was carried out in a regular glass tube, and after the reaction was over (complete termination of fumes), the contents were extracted with MeOH-$d_4$, filtered, transferred to an NMR tube and analyzed. Table 2 describes decontamination efficacy (%) and time.

TABLE 2

Decontamination efficacies

| Compound | VX | HD |
|---|---|---|
| 1 | >99% in 1 h | >99% in 1 day |
| 2 | | |
| 3 | | |
| 4 | | |
| 6 | >99% in 1 h | >99% in 2 hours |
| 8 | 77% in 5 days | >99% in 1 day |
| 11 | No VX in extraction | |
| 13 | >99% in 1 h | >99% in 2 hours |
| 15 | 96% in 1 day | >99% in 1 h |
| 17 | >99% in 0.5 h | >99% in 0.5 h |
| 20 | >99% in 1 day | >99% in 1 h |
| 21 | >99% in 0.5 h | >99% in 0.5 h |
| 24 | >99% in 0.5 h | >99% in 0.5 h |
| 25 | >99% in 0.5 h | >99% in 0.5 h |
| 27 | >99% in 0.5 h | >99% in 0.5 h |
| 30 | >99% in 0.5 h | >99% in 0.5 h |

As expected, the major decontamination product for VX was the non-toxic product ethyl methylphosphonic acid (EMPA). For sulfur mustard, decontamination products usually include hydrolysis products, such as thiodiglycol (TDG), oxidation products, such as sulfur mustard sulfoxide or sulfone, or elimination products, such as divinyl sulfide (DVS) [16]. However, analyzing decontamination products of the reaction between halamines and sulfur mustard revealed that, in this case, a different mechanism takes place and multi-chlorinated compounds are produced (Scheme 13). As we found out, in the case of no evident violent reaction, oxidation to the sulfoxide occurs as the initial step, followed by excess chlorination takes place mainly on the a methylene (adjacent to the sulfoxide). When a violent reaction is evident, no oxidation happens, and excess chlorination occurs on the terminal methylene (adjacent to the existing chlorine atom). The difference in chlorination sites are attributed to shifting acidities of the methylene hydrogens, during the oxidation of sulfide to sulfoxide. These findings are consistent with the limited information given in the literature [18].

Scheme 13. Proposed mechanism leading to multichlorinated products

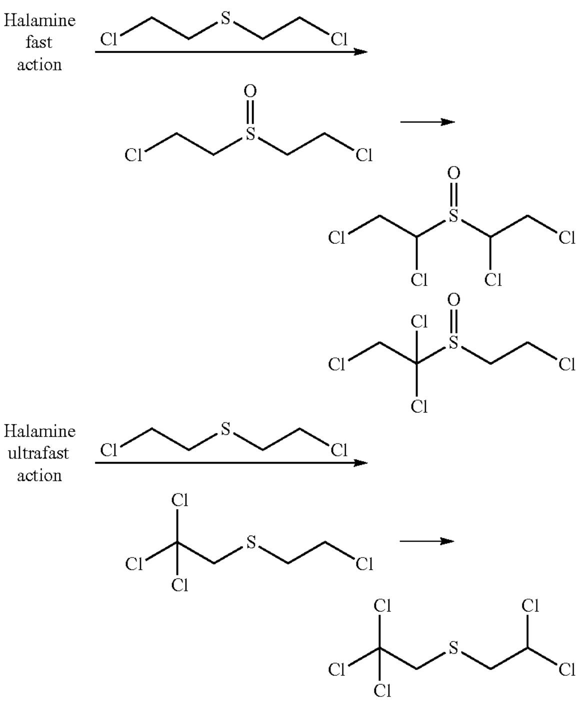

EXAMPLE 9

Decontamination of Biological Agents

Figure 4B:
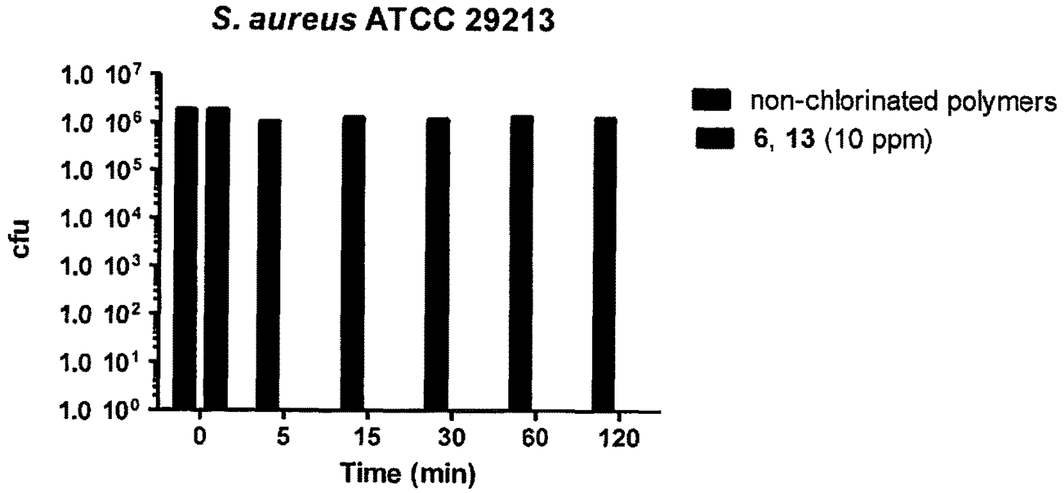

Halamines are well known in their capacity to efficiently kill bacteria. Nevertheless, since the melamine-derived halamines are novel compounds, we tested two of them against bacteria, to ascertain that they exhibit the same behavior. Later, we tested all new melamine halamines against *Bacillus anthracis*, as a worst-case screen. In the first test, chlorinated and non-chlorinated polymers 6 and 13 (10 ppm each) were tested against *E. coli* ATCC 25922 ($2.9\times10^6$ CFU) and *S. aureus* ATCC 29213 ($1.9\times10^6$ CFU). Non-chlorinated polymers gave no effect at all, while both chlorinated polymers showed 6-log kill within 5 minutes (FIGS. 4A and 4B).

Figure 5A:
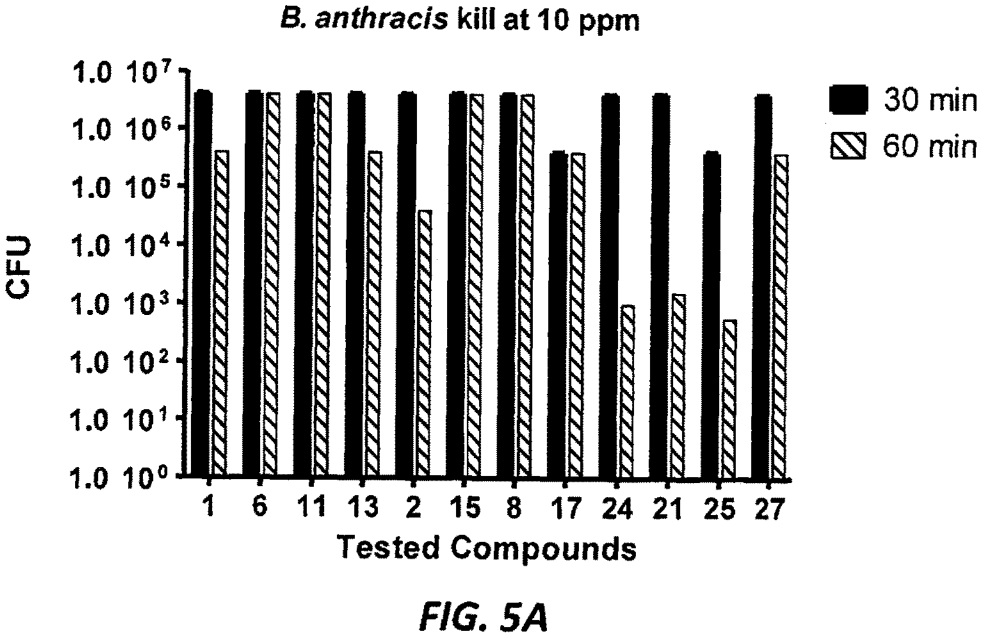
FIGS. 5A and 5B are graphs showing the killing efficiency of the compounds of the invention towards *B. anthracis* at 10ppm (5A) and 100ppm (5B)
Figure 5B:
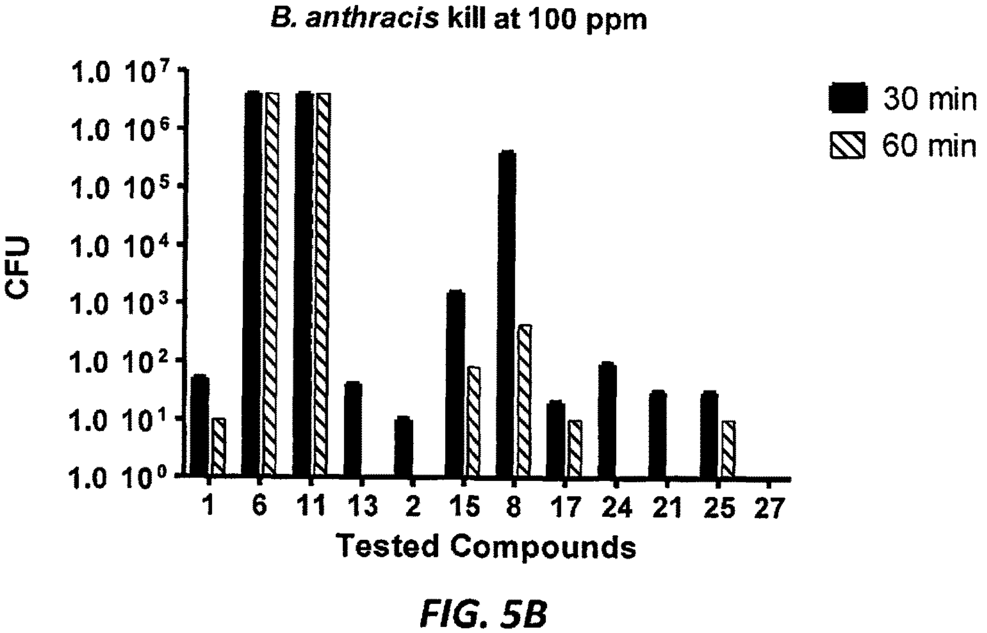
Figure 6A:
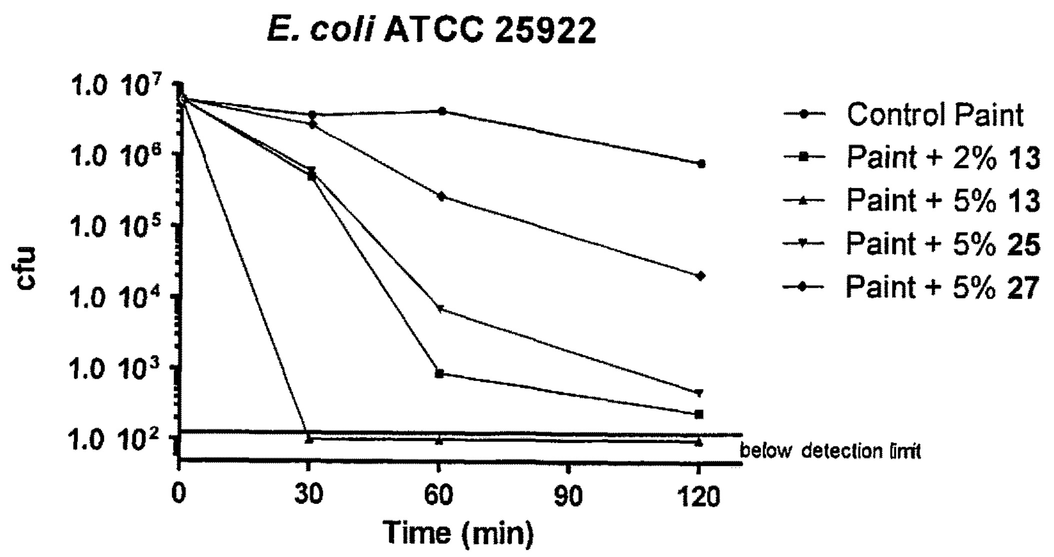
FIGS. 6A and 6B are graphs showing the biocidal efficiency of a paint comprising the compounds of the invention towards *E. coli* (6A) and *S. aureus* (6B)
Figure 6B:
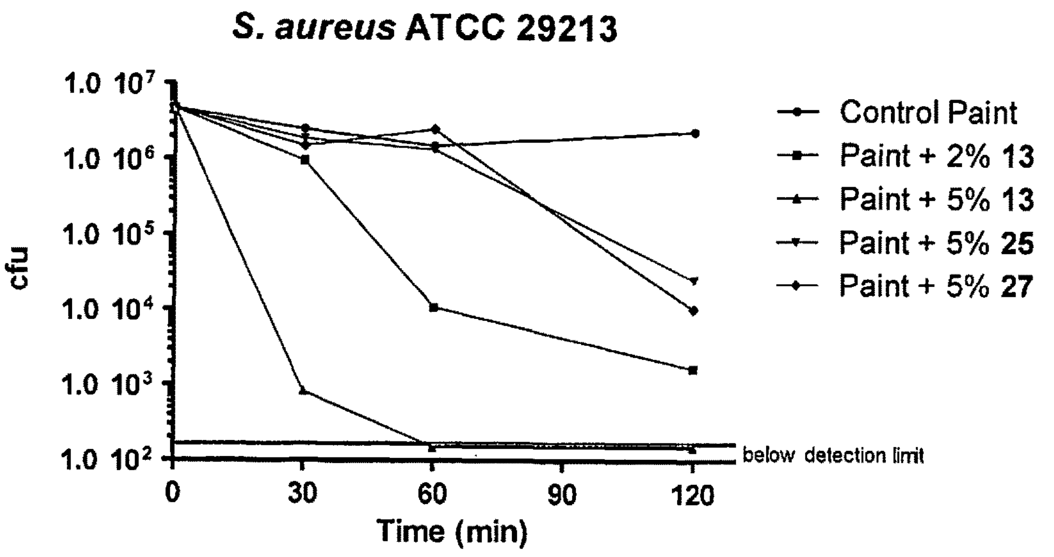
Figure 7A:
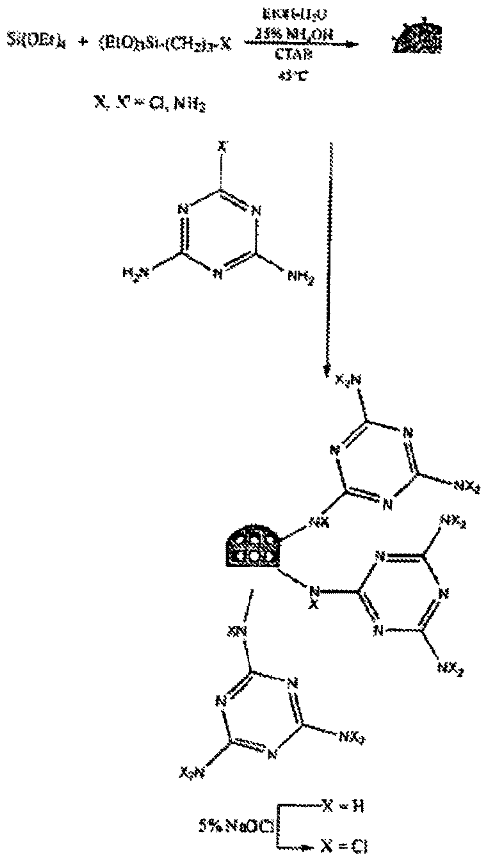
FIGS. 7A and 7B illustrate exemplary embodiments of the invention.
Figure 7B:
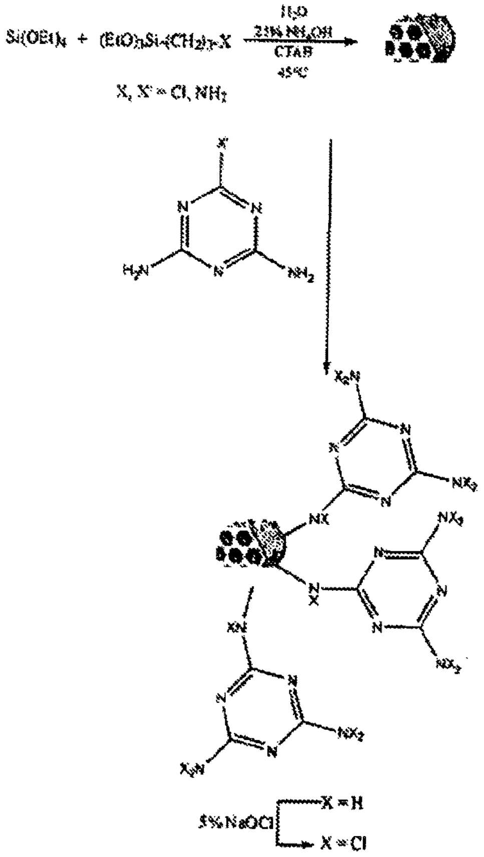

Since these model compounds showed strong activity against bacteria, *Bacillus anthracis*, a more robust challenge was used for the screening of novel melamine-derived halamines. The initial test comprised of reacting $4\times10^6$ spores with 10 or 100 ppm of tested halamines. Most of the halamines at 100 ppm concentration exhibited 6-log kill after 1 hour, and 5-log kill within 30 minutes (FIGS. 5A and 5B).

The efficacy of halamines to decontaminate *Bacillus* spores was presented previously only once. A group at the University of California at Davis, in collaboration with the HaloSource company showed that *Bacillus subtilis* (an anthrax surrogate) was placed on textiles treated with hydantoin-derived halamine (FIG. 3). The percent reduction in live spores was around 100% in 48 hours, depending on the fabric used [19].

It is noteworthy that compound 11 is derived from commercial poly methacrylamide and does not contain a melamine moiety. It was tested as a negative control, since it did not exhibit good decontaminating results against sulfur mustard or VX.

While the invention has been described using some specific examples, many modifications and variations are possible. It is therefore understood that the invention is not intended to be limited in any way, other than by the scope of the appended claims.

EXAMPLE 10

N-halamine Melamine Coated/Bound Nanoparticles

This family is based on commercial functionalized silica or synthesized silica nanoparticles. The melamine moieties are either covalently bound to a functional group on the silica core, or serves as a coating of the silica core. These silicone-based melamine halamines are suited to be incorporated into surfaces (e.g. polymeric sheets, silicone products) or may be used as coatings. Some examples are described in the following schemes:

A. Binding melamine onto commercial propionyl chloride functionalized silica

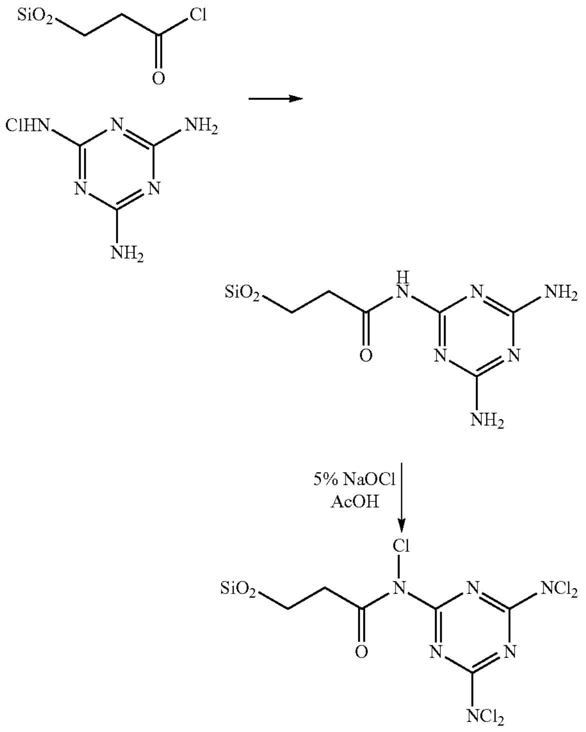

B. Preparation of silica nanoparticles and coating with melamine-methacrylate co-polymers

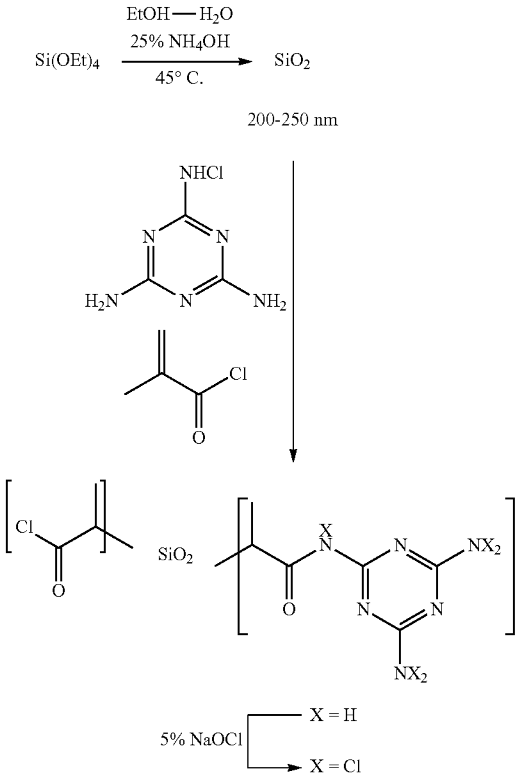

D. Preparation of silica polymer bearing melamine halamine moieties

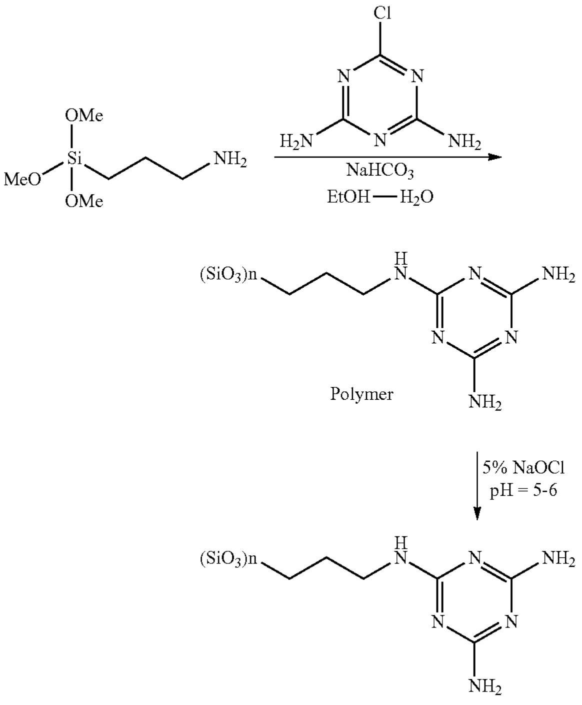

EXAMPLE 11

Biocidal Efficacy Test for Melamine-Halamine Containing Paint

Test samples were prepared by first preparing melamine-halamine containing paints: 4 mL matt polyurethane paint was mixed with 0.25 mL thinner containing varying amounts (2-5%) of various chlorinated melamine-halamine compounds (compounds 13, 25 or 27, see table below). Transparency sheets were painted with original and melamine-halamine containing paint and following drying, they were cut into 2.5×2.5 cm rectangles. Original paint samples and melamine-halamine paint samples were challenged with *Staphylococcus aureus* (ATCC 29213) and *Escherichia coli* (ATCC 25922). A "sandwich test" was employed to evaluate the efficacies of the chlorinated samples. For a typical test, 25 μL of the bacterial suspension was placed in the center of a sample in a sterile Petri dish and covered with a second identical size of sample. After contact times of 30, 60, and 120 min, the samples were placed (back to back) in sterile conical centrifuge tubes containing 5.0 mL of a 0.02 N sodium thiosulfate solution to quench any oxidative chlorine and vortexed for 2 min. The samples were then removed, and the quenched solution was diluted serially with 100 mM phosphate buffer, pH 7 ($10^{-1}$, $10^{-2}$, $10^{-3}$). Then, 4 drops of 10 μL of original and each diluted solution were placed on a BHIA plate. The plates were incubated at 37° C. for 24 h, and then bacterial colonies were counted for further analysis.

TABLE 3

| Biocidal efficacies | | | | | |
|---|---|---|---|---|---|
| | | *E. coli* ATCC 25922 | | *S. aureus* ATCC 29213 | |
| Sample | Contact Time (min) | Total Bacterial Concentration (cfu/mL) | Log reduction | Total Bacterial Concentration (cfu/mL) | Log reduction |
| Original | 0 | $6.19 \times 10^6$ | 0 | $4.47 \times 10^6$ | 0 |
| | 30 | $3.75 \times 10^6$ | 0.22 | $2.53 \times 10^6$ | 0.27 |
| | 60 | $4.38 \times 10^6$ | 0.15 | $1.52 \times 10^6$ | 0.50 |
| | 120 | $8.41 \times 10^5$ | 0.87 | $2.38 \times 10^6$ | 0.30 |
| 2% | 0 | $6.19 \times 10^6$ | 0 | $4.47 \times 10^6$ | 0 |
| compound | 30 | $5.00 \times 10^5$ | 1.09 | $9.70 \times 10^5$ | 0.69 |
| V | 60 | $8.75 \times 10^2$ | 3.85 | $1.10 \times 10^4$ | 2.63 |
| (13) | 120 | $2.50 \times 10^2$ | 4.39 | $1.67 \times 10^3$ | 3.45 |
| 5% | 0 | $6.19 \times 10^6$ | 0 | $4.47 \times 10^6$ | 0 |
| compound | 30 | $1.25 \times 10^2$ | 4.70 | $8.33 \times 10^2$ | 3.75 |
| V (13) | 60 | Below detection limit (125) >4.7 log reduction | | Below detection limit (167) >4.4 log reduction | |
| | 120 | Below detection limit (125) >4.7 log reduction | | Below detection limit (167) >4.4 log reduction | |
| 5% | 0 | $6.19 \times 10^6$ | 0 | $4.47 \times 10^6$ | 0 |
| compound | 30 | $6.02 \times 10^5$ | 1.01 | $1.89 \times 10^6$ | 0.40 |
| II | 60 | $7.13 \times 10^3$ | 2.94 | $1.35 \times 10^6$ | 0.55 |
| (25) | 120 | $5.00 \times 10^2$ | 4.09 | $2.57 \times 10^4$ | 2.27 |
| 5% | 0 | $6.19 \times 10^6$ | 0 | $4.47 \times 10^6$ | 0 |
| compound | 30 | $2.75 \times 10^6$ | 0.35 | $1.53 \times 10^6$ | 0.49 |
| III | 60 | $2.73 \times 10^5$ | 1.36 | $2.52 \times 10^6$ | 0.28 |
| (27) | 120 | $2.25 \times 10^4$ | 2.44 | $1.02 \times 10^4$ | 2.67 |

BIBLIOGRAPHY

1. Worley, S. D., Wojtowicz, J. A. N-Halamines. Kirk-Othmer Encyclopedia of Chemical Technology, 5th edition 2005, vol. 13, 98-122. John Wiley and Sons, Inc. and references therein.

2. Speck, J. C. Polychloro-7,8-disubstituted-2,5-diimino glycouril for use as an anti-vesicant. U.S. Pat. No. 2,885,305, 5 May 1959.
3. A. Shih, M. L., Korte, W. D., Smith, J. R., Szafraniec, L. L. Reactions of sulfides with S-330, a potential decontaminant of sulfur mustard in formulations. J. Appl. Toxicol. 1999, 19, S83-S88.
B. Shih, M. L., Korte, W. D., Smith, J. R., Szafraniec, L. L. Analysis and stability of the candidate sulfur mustard decontaminant S-330. J. Appl. Toxicol. 1999, 19, S89-S95.
4. Worley, S. D. Method for decontamination of toxic chemical agents. U.S. Pat. No. 4,874,532, Oct. 17, 1989.
5. Yang, Y.-C., Baker, J. A., Ward, J. R. Decontamination of chemical warfare agents. Chem. Rev. 1992, 92, 1729-1743.
6. Boone, C. M. Present state of CBRN decontamination methodologies. TNO report, TNO-DV 2007 A028.
7. Hui, F., Debiemme-Chouvy, C. Antimicrobial N-halamine polymers and coatings: a review of their synthesis, characterization, and application. Biomacromolecules 2013, 14, 585-601 and references therein.
8. Sun, G., Broughton, R. Jr. Chemistry of functional finishing: self-decontaminating textile materials. National Textile Center Research Briefs—Chemistry Competency: June 2004.
9. Fei, X., Sun, G. Oxidative degradation of organophosphorous pesticides by N-halamine fabrics. Ind. Eng. Chem. Res. 2009, 48, 5604-5609.
10. Ren, X., Akdag, A., Kocer, H. B., Worley, S. D., Broughton, R. M., Huang, T. S. N-Halamine-coated cotton for antimicrobial and detoxification applications. Carbohydrate Polymers 2009, 78, 220-226.
11. Arsem, W. C. Active halogen compounds and processes for their production. U.S. Pat. No. 2,472,361, Jun. 7, 1949.
12. Bann, B., Miller, S. A. Melamine and derivatives of melamine. Chem. Rev. 1958, 58(1), 131-172.
13. Graichen, S. Melamine-polycarboxylic acid amides and their use as anticorrosive agents. U.S. Pat. No. 6,096,244, Aug. 1, 2000.
14. Gupta, R. B. Process for preparing amide derivatives from halomines and acid halides. EP Patent Appl. 0541966, Oct. 12, 1992.
15. Vogel's textbook of quantitative chemical analysis. Jeffery, G. H., Bassett, J., Mendham, J., Denney, R. C. 5th Edition, 1989, Longman Scientific & Technical Ed. UK, pp. 396-397.
16. A. Mizrahi, D. M., Columbus, I., 31P MAS NMR: A useful tool for the evaluation of VX natural weathering in various urban matrixes. Environ. Sci. Tech. 2005, 39, 8931-8935.
B. Mizrahi, D. M., Goldvaser, M., Columbus, I. Long-term evaluation of the fate of sulfur mustard on dry and humid soils, asphalt, and concrete. Environ. Sci. Tech. 2011, 45, 3466-3472.
C. Columbus, I., Waysbort, D., Marcovitch, I., Yehezkel, L., Mizrahi, D. M. VX fate on common matrices: evaporation versus degradation. Environ. Sci. Tech. 2012, 46, 3921-3927.
17. Reiff, L. P., Taber, D. F., Yet, L. In Proceedings of the 1996 Scientific Conference on Chemical and Biological Defense Research, ERDEC-SP-048, U.S. Army ERDEC, Aberdeen Proving Ground, Aberdeen, Md. 1997; pp. 799.
18. A. Dubey, D. K., Malhotra, R. C., Vaidyanathaswamy, R., Vijayaraghavan, R. Reaction of bis(2-chloroethyl) sulfide with N,N-dichlorobis(2,4,6-trichlorophenyl)urea. J. Org. Chem. 1999, 64, 8031-8033.
B. Bartram, P. W., Wagner, G. W., Maclver, B. K., Rohrbaugh, D. K. Preliminary studies on the decomposition of bis(2-chloroethyl)sulfide absorbed on vermiculite. In Proceedings of the 1997 ERDEC scientific conference on chemical and biological defense research, ERDEC-SP-063, Nov. 1997, 623-627
19. Sun, G. Biocidal technology for reusable and disposable textiles. Presentation at University of California, Davis, 2007.

The invention claimed is:

1. A multihalogenated N-halamine compound or a salt thereof comprising at least two halogenated melamine moieties having formula(V):

(V)

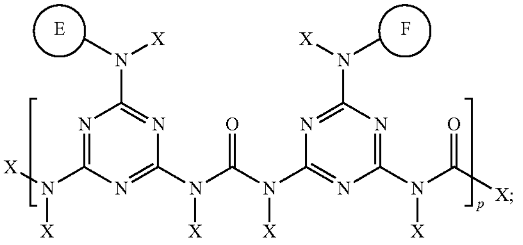

wherein E and F are independently selected from hydrogen, halogen, —C(═O)—N(halogen)-melamine; X is a halogen selected from Cl, Br, I and F; and p is selected from 1 to 20.

2. A compound according to claim 1 of formula (V') or a salt thereof:

(V')

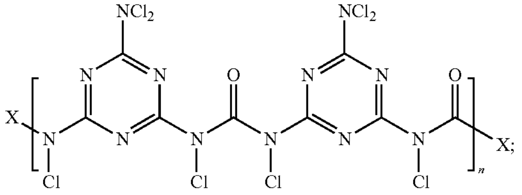

wherein p is selected from 1 to 20.

3. A compound according to claim 1 of formula (V") or a salt thereof:

(V")

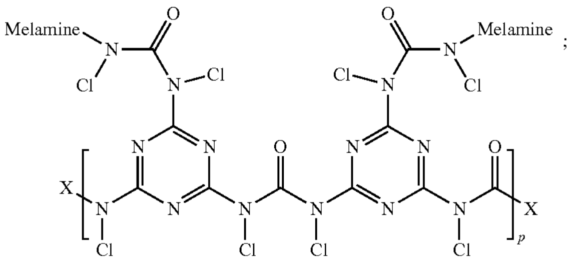

wherein p is selected from 1 to 20.

4. A compound according to claim 1, wherein the N-halamine bonds are regenerated by contacting said compound with hypochlorite, hypobromite, hypoiodite, or hypofluorite.

5. A composition comprising a compound according to claim 1 or a salt thereof and at least one ingredient selected from the group consisting of solvents, diluents, binders, resins, polymers, fillers, pigments, dyes, wetting agents, catalysts, thickeners, stabilizers, emulsifiers, texturizers, adhesion promoters, UV stabilizers, flatteners, and biocides.

6. A composition according to claim 5, wherein said composition is selected from a paint, a plastic material, a silicone-based material, a textile, or a coating.

7. A composition according to claim 5, wherein said composition is for use in columns for water treatment.

8. A compound according to claim 1, for use as a decontaminating agent for deactivating a chemical agent and/or neutralizing a biological agent.

9. A compound for use according to claim 8, wherein the chemical agent and/or biological agent is selected from a chemical warfare agent (CWA), particularly sulfur mustard (HD) or O-ethyl-S-2-(N,N-diisopropylamino)ethylmethylphosphonate (VX), or mold or mildew, or a bacterial agent, particularly *Escherichia coli, Staphylococcus aureus* or *Bacillus anthracis.*

10. A method for decontaminating or preventing the contamination of a material by a chemical agent and/or a biological agent, said method comprising incorporating into said material or coating onto said material an effective amount of a compound according to claim 1.

* * * * *